US00RE34692E

United States Patent [19]

Becher

[11] E Patent Number: Re. 34,692

[45] Reissued Date of Patent: Aug. 9, 1994

[54] TRANSDERMAL THERAPEUTIC SYSTEM

[75] Inventor: Frank Becher, Koblenz, Fed. Rep. of Germany

[73] Assignee: LTS Lohmann Therapi-Systeme GmbH & Co. KG, Neuwied, Fed. Rep. of Germany

[21] Appl. No.: 5,732

[22] PCT Filed: Jun. 21, 1988

[86] PCT No.: PCT/DE88/00370

§ 371 Date: Apr. 3, 1989

§ 102(e) Date: Apr. 3, 1989

[87] PCT Pub. No.: WO89/00437

PCT Pub. Date: Jan. 26, 1989

Related U.S. Patent Documents

Reissue of:

[64] Patent No.: 5,066,494
Issued: Nov. 19, 1991
Appl. No.: 327,810
Filed: Jun. 21, 1988

[51] Int. Cl.[5] ..... A61F 13/02

[52] U.S. Cl. ..... 424/448; 424/447; 424/449

[58] Field of Search ..... 424/448, 449, 447

[56] References Cited

U.S. PATENT DOCUMENTS 4,666,441 5/1987 Andriola et al. ..... 424/449
4,822,617 4/1989 Panoz ..... 424/449

FOREIGN PATENT DOCUMENTS 930668 7/1973 Canada .

*Primary Examiner*—Thurman K. Page
*Assistant Examiner*—James M. Spear
*Attorney, Agent, or Firm*—Kalish & Gilster

[57] ABSTRACT

The invention relates to a transdermal therapeutic system for administering or applying active substances to the skin with a backing layer remote from the skin, an active substance depot, an active substance delivery control means controlling the delivery of the active substance through the system and a [contact] *pressure sensitive* adhesive means for fixing the therapeutic system to the skin, in which the active substance depot is a multichamber system, in which discreet chambers contain one or more active substances.

15 Claims, 3 Drawing Sheets

TRANSDERMAL THERAPEUTIC SYSTEM

Matter enclosed in heavy brackets [ ] appears in the original patent but forms no part of this reissue specification; matter printed in italics indicates the additions made by reissue.

BACKGROUND AND SUMMARY OF THE INVENTION

The invention relates to a transdermal therapeutic system for the administration of active substances to the skin with a backing layer remote from the skin, an active substance depot, an active substance delivery control device controlling the delivery of the active substance through the system and a [contact] *pressure sensitive* adhesive fixing means for the therapeutic system to the skin, and to the use thereof.

Such transdermal systems with several active substances depots are e.g. known from P 36 29 404.0, in which one or more isolated active substance depots, which are not interconnected, are arranged in an active substance distribution matrix.

This known arrangement is particularly preferred for solid or very viscous materials, the highly concentrated active substance permeating into the active substance distribution matrix and from there flows onto the optionally [contact] *pressure sensitive* adhesive control membrane.

In the case of flowable active substances or active substance formulations, the active substance is frequently received in bag-like recesses of a matrix or in a bag formed by a controlling membrane or a film. When the active substance reservoir is exhausted, there is a rapid decrease in the internal pressure and of the migration speed of the active substance, too. Another disadvantage of systems with large bag-like units with a fluid active substance formulation is that they are sensitive to pressure and on the system being loaded by pressure, the complete active substance passes uncontrollably out of a burst bag into the active substance distribution matrix and the delivery of the active substance to skin then no longer takes place in controlled form. This is particularly undesired if it is a highly effective active substance, whose overdosing leads to risks.

Another disadvantage of the known systems is that they cannot be subdivided, e.g. for children and adults requiring less active substance different sizes have to be kept in stock.

Finally, in the case of a plaster with a larger liquid reservoir, as a result of gravity action a non-uniform distribution of the liquid occurs, which significantly impairs the uniformity of active substance delivery.

The problem of the present invention is therefore to avoid the aforementioned disadvantages of the prior art and to provide a novel transdermal therapeutic system, which permits more reliable handling, particularly of liquid active substances or active substance formulations.

According to the invention this problem is solved by a transdermal therapeutic system, which is characterized in that the active substance depot is a multichamber system, in which discrete chambers have one or more active substances.

A multichamber system is advantageous, because the distribution of the active substance is better and possibly the cutting off or separating of part of the transdermal therapeutic system does not lead to the flowing or dropping out of the complete active substance formulation. Furthermore, flowable active substance formulations can only move to a limited extent under the action of gravity or pressure, so that even under the influence of gravity a relatively uniform distribution of an active substance-containing liquid can be obtained. If as a result of pressure loading an active substance chamber bursts, the remaining chambers remain undamaged, so that the function of the system is to a certain extent maintained, which is a precautionary measure reducing overdosing risks in the case of highly effective liquid active substances.

An advantageous further development of the inventive concept consists of the individual chambers being at least partly interconnected by channels in such a way that a flow of the chamber content for pressure compensation purposes is possible.

It can be advantageous for the connecting channels between the chambers to have an internal diameter such that they permit the through flow of the active substance fluid only when pressure is applied. This embodiment avoids the bursting of the depot and therefore to the system being made unusable under pressure loading, e.g. on application to animals in veterinary medicine such a pressure distributing means is useful.

It is also possible for the multichamber system to be purely a channel system.

The chambers can in each case have optionally different active substance delivery control means. This embodiment is particularly appropriate if different active substances are used in a system, in which said active substances are to be supplied to the skin with different delivery rates.

The chambers can be arranged in one or more identical or different active substance distribution matrices, which can be superimposed and/or juxtaposed.

An inventive transdermal therapeutic system preferably has an interrupted or uninterrupted [contact] *pressure sensitive* adhesive layer as the fixing means to the skin.

The transdermal therapeutic system can also have one or more [contact] *pressure sensitive* adhesive layers between the backing layer and the fixing device. This is particularly necessary and appropriate if the active substance distribution matrix is not [contact] *pressure sensitive* adhesive and the non-permeable backing layer can only be applied via a further [contact] *pressure sensitive* adhesive layer.

The inventive system is particularly advantageously used with a liquid active substance or substances, or in solution.

In multichamber systems, desired breaking lines can be provided between individual chambers and optionally in the backing layer and other layers. Such desired breaking lines permit a division of the system if a smaller active substance delivery is desired. This can e.g. avoid expensive storage of transdermal systems of different sizes and doses.

The chambers can be arranged at different height levels of the plaster, optionally in different distribution matrixes. The multichamber system can be arranged in a [contact] *pressure sensitive* adhesive active substance distribution and control matrix.

The multichamber system can comprise active substance or active substance solution-filled films with control action, which are permeable for the active substance, optionally also in controlling manner and which are welded together to form a multichamber system.

The inventive therapeutic system can be used for the packing and administration of transcutaneously applicable active substances for human and veterinary medicine, as well as in cosmetics.

The depot can also have inert adjuvants. The term "inert" is here understood to mean that active substance and adjuvant do not react with one another. An "inert" adjuvant can also be a substance having physiological effects, such as e.g. DMSO or the like, which e.g. increases the permeability of the skin. The adjuvants can also be constituted by support materials, which make the active substance depot insensitive with respect to pressure and tension application, as well as carriers.

It is possible to use active substances which can be applied in transdermal manner and typical examples of these ar given below.

Nicotine

Corticosteroids:

hydrocortisone, prednisolone, beclomethasone-proprionate, flumethasone, triamcinolone, triamcinoloneacetonide, fluocinolon, fluocinolin-acetonide, fluocinolon-acetonide-acetate, clobetason-proprionate, etc.

Analgesics, anti-inflammatory agents:

acetaminophen, mefenamic acid, flufenamic acid, diclofenac, diclofenac-sodium-alclofenac, oxyphenbutazone, phenylbutazone, ibuprofen, flurbiprofen, salicyclic acid, 1-menthol, camphor, sulindac-tolmetin-sodium, naproxen, fenbufen, etc.

Hypnotically active sedatives:

phenobarbital, amobarbital, cyclobarbital, triazolam, nitrazepam, lorazepam, haloperidol, etc.

Tranquilizers:

fluphenazine, thioridazine, lorazepam, flunitrazepam, [chloropromazine] *chlorpromazine*, etc.

Antihypertensives:

pindolol, bufralol, indenolol, nifedipine, lofexidin, nipradinol, bucumolol, etc.

Antihypertensively acting diuretics:

hydrothiazide, bendroflumethiazide, cyclobenthiazide, etc.

Antibiotics:

penicillin, tetracycline, oxytetraccline, fradiomycin-sulpbate, erythromycin, chloramphenicol, etc.

Anesthetics:

lidocaine, benzocaine, ethylaminobenzoate, etc.

Antimicrobiological agents:

benzalkonium chloride, nitrofurazone, nystatin, acetosulfamine, clotrimazole, etc.

Antifungal agents:

pentamycin, amphotericin B, pyrrolnitrin, clotrimazole, etc.

Vitamins:

vitamin A, ergocalciferol, [chlolecalciferol] *cholecalciferol*, octotiamine, riboflavin butyrate, etc.

Antiepileptics:

nitrazepam, meprobamate, clonazepam, etc.

Coronary vasodilators:

nytroglycerol, dipyridamole, erythritol tetranitrate, pentaerythritol tetranitrate, propatyinitrate, etc.

Antihistamines:

diphenyl hydromine hydrochloride, chlorpheniramine, diphenylimidazole, etc.

Antitussives:

[dertromethorphan] *dextromethorphan* (hydrobromide), terbutaline (sulphate), ephedrine (hydrochloride), [salbutanol] *albuterol* (sulphate), isoproterenol (sulphate, hydrochloride), etc.

Sexual hormones:

progesterone, etc.

Thymoleptics:

doxepin, etc.

Further medicaments/pharmaceuticals:

5-fluorouracil, fentanyl, desmopressin, [domperdon] *domperidon*, scopolamine (hydrobromide), peptide, etc.

Obviously this list is not exhaustive.

Advantageously the active substance matrix can be built up in layer form, the layers being the same or different. The active substance matrix can be [contact] *pressure sensitive* adhesive and can e.g. be a rubber material, such as styrene/isoprene/styrene block copolymers, silicone rubber or synthetic resins, such as poly(meth)acrylate, polyurethane, polyvinylether, polyester, etc—a list of suitable matrix materials appearing e.g. in DE-OS 3500 508, to which reference is made. It can be advantageous if the reservoir matrix is [contact] *pressure sensitive* adhesive, because this can obviate the need for providing a separate [contact] *pressure sensitive* adhesive fixing device in the system. The use if such a [contact] *pressure sensitive* adhesive matrix is inter alia dependent on the compatibility of the matrix material with the active substance. [contact] *Pressure sensitive* adhesive matrix materials are known.

Preferred non-[contact] *pressure sensitive* adhesive matrix materials are polymers comprising poly(meth)acrylate, polyvinylpyrrolidone, ethylcellulose, hydroxypropylcellulose, hydroxypropylmethylcellulosephthalate, polyvinylalcohol or copolymers thereof with vinyllaurate or maleic acid, vinylacetate or copolymers thereof with vinyllaurate or maleic acid; polyvinylether, butyl rubber and polycaprolactam.

For example the chambers can also be provided between a back-side reservoir matrix layer and a skin-side reservoir matrix layer.

The backing layer can be constituted by per se known active substance-impermeable materials, such as metal foils, plastic films or laminates thereof, as are well known to the expert.

Further features and advantages can be gathered from the following description of non-limitative embodiments and with reference to the attached drawings, wherein show:

FIG. 1 an inventive therapeutic system in cross-section.

FIG. 2 another inventive system in cross-section.

FIG. 3 another inventive system in cross-section.

FIG. 4 an inventive system with channels in plan view of the system with the backing layer removed.

FIG. 5 another inventive embodiment in plan view of the system with the backing layer removed.

FIG. 6 another embodiment of the invention in cross-section.

FIG. 7 another embodiment of the invention with the backing layer removed and with a channel system.

FIG. 8 an embodiment of an inventive system with a nonplanar channel system in cross-section.

FIG. 9 another transdermal system according to the invention in cross-section.

FIG. 10 an embodiment of the invention in plan view with the backing layer removed and with desired breaking lines.

DESCRIPTION OF THE PREFERRED EMBODIMENTS

FIG. 1 shows in cross-section a first preferred embodiment of an inventive plaster-like transdermal system. The system has an active substance-impermeable backing layer 10, such as a metal foil or a plastic film, or a laminate of different materials. Beneath the backing layer 10 is located the active substance distribution matrix 12 formed from a material permeable to the active substance. For example self-cross-linking acrylate copolymers are suitable for such an active substance distribution matrix, which is preferably [contact] *pressure sensitive* adhesive in this embodiment. However, the matrix is dependent on the active substance used. Chambers 14 for the active substance are formed in the matrix and are filled with a liquid active substance, such as a nicotine solution. Between the individual chambers 14, the two active substance layers stick together and thus prevent the free flow of nicotine solution in the entire chamber system 14. The active substance, here nicotine, is dissolved in the matrix and the liberation rate of the transdermal system is inter alia determined by the diffusion rate of the active substance in the active substance matrix. Below the active substance matrix, which here completely surrounds the chambers 14, is applied a [contact] *pressure sensitive* adhesive layer 19, which is suitable for fixing the system to the skin. This [contact] *pressure sensitive* adhesive layer is also permeable for the active substance and can optionally have a controlling action on the active substance delivery to the skin.

FIG. 2 shows a further preferred embodiment of an inventive plaster-like, transdermal therapeutic system in cross-section and in this case different chambers 14', 14 are formed in two different active substance matrixes 12, 12', which can e.g. contain different active substances or different active substance formulations. The two active substance matrices can be chosen in accordance with requirements of the particular active substance delivery speed. The system has an uninterrupted adhesive layer 19 for application to the skin or for fixing the system to the skin, the adhesive also having a certain control effect.

Figure 1:
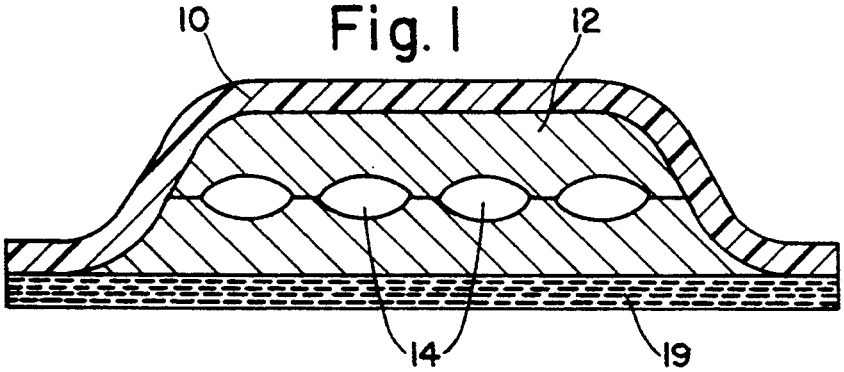
Figure 2:
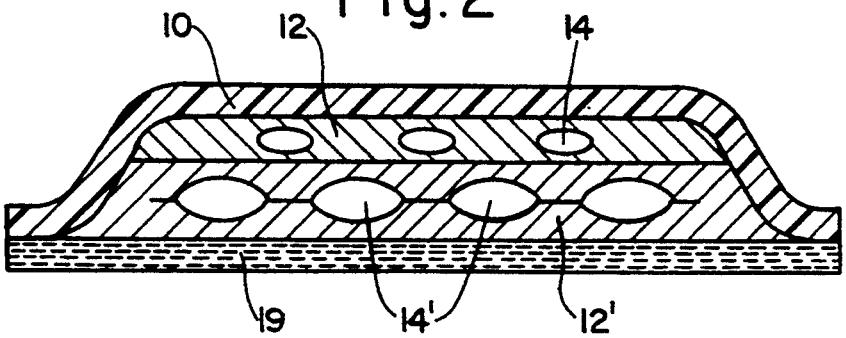
Figure 3:
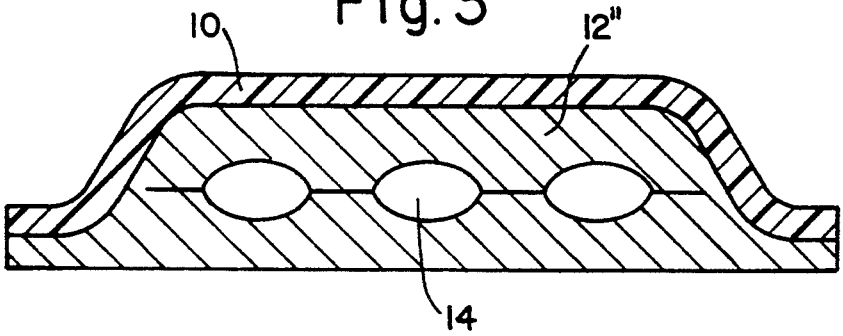
FIG. 3 shows an easy to manufacture inventive embodiment, in which the chambers 14 are formed in a [contact] *pressure sensitive* adhesive active substance matrix 12' adhesion characteristics of which are also adequate for fixing the system to the skin.
Figure 4:
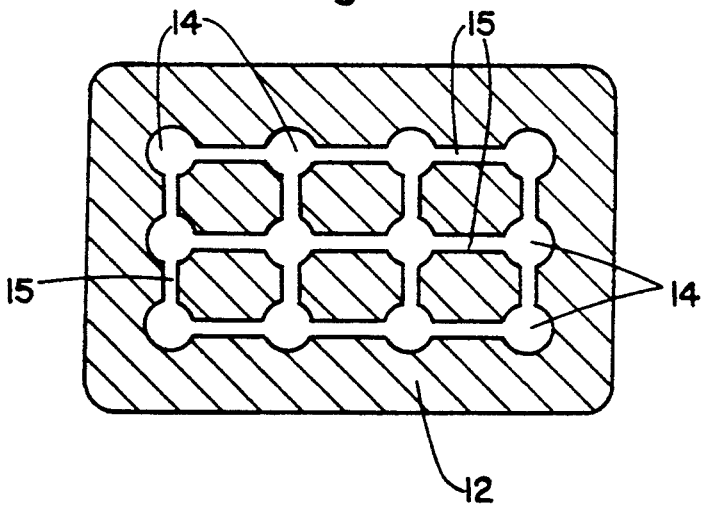
FIG. 4 shows another preferred embodiment of an inventive transdermal therapeutic system, in which the active substance chambers 14 are interconnected by channels, so that e.g. in the case of local pressure application to the system the active substance-containing liquid contained in the channel system/chambers 14 can flow for pressure compensation purposes.
Figure 5:
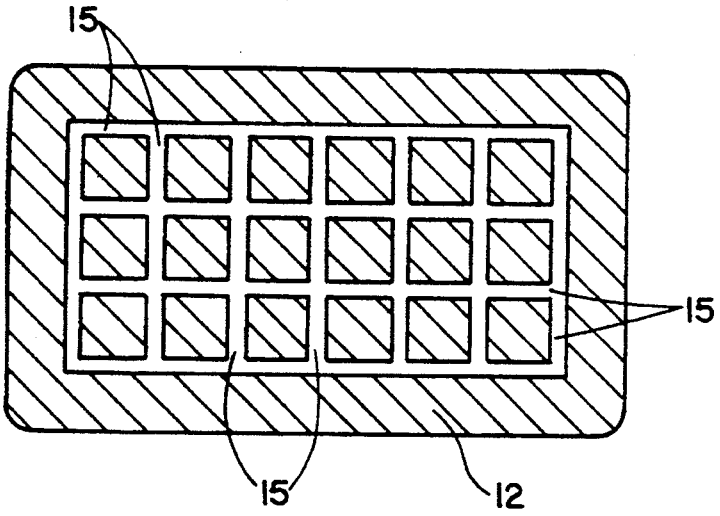
FIG. 5 shows an inventive system, in which the multichamber system comprises channels 15 with active substance arranged in lattice-like manner. Here again the backing layer 10 of the system is removed, so that it is possible to see the active substance depots.
Figure 6:
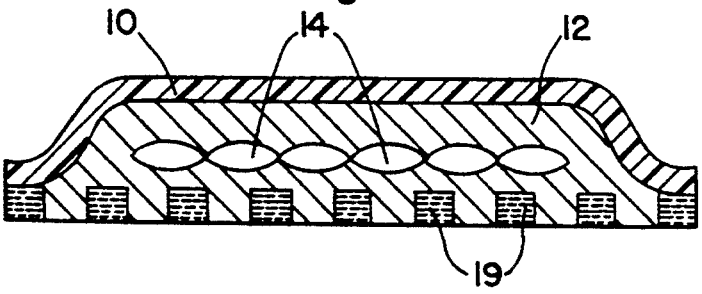
FIG. 6 shows an embodiment of the invention, in which the individual adhesive regions 19 are arranged in the active substance matrix 12, in order to fix the system to the skin, whilst the active substance delivery in this case mainly takes place vie the non-adhering or slightly adhering active substance matrix surfaces.
Figure 7:
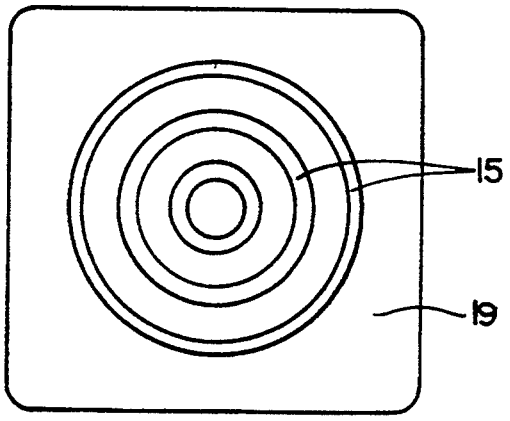
FIG. 7 shows an embodiment with concentric, channel-like chambers 14 and there can also be different active substances in the individual ring channels 14.
Figure 8:
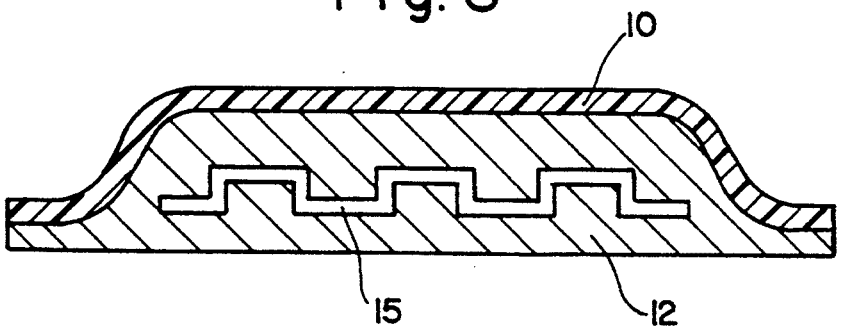

FIG. 8 shows another embodiment of a system, which is similar to that of FIG. 3 in that once again a [contact] *pressure sensitive* adhesive active substance matrix is used, in that here a channel system 15, which contains the active substance or a liquid containing the latter is provided. This arrangement is e.g. advantageous if the plaster is exposed to pulling or tension movements, whereby tearing would occur in the case af a flat channel system without a "tension reserve".

Figure 9:
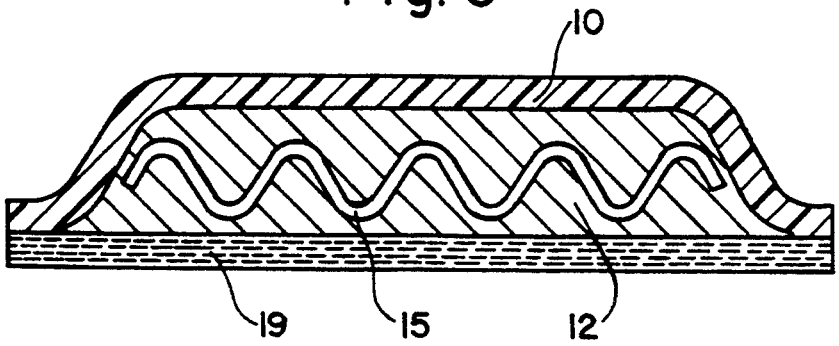

FIG. 9 shows a similar arrangement, in which the plaster has an additional [contact] *pressure sensitive* adhesive layer 10 for fixing the system to the skin and optionally additional control of the active substance delivery.

Figure 10:
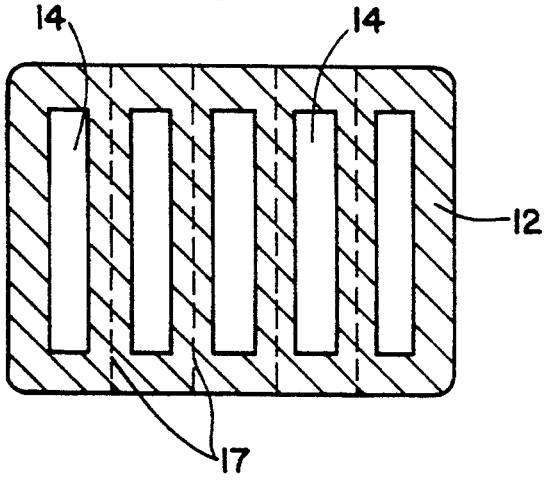

FIG. 10 shows an arrangement with strip-like active substance depots 12. The drawing is a plan view of the inventive system after removal of the backing layer 10. It is possible to see the desired breaking lines 17, which are usable for the random reduction/dose change of the system. This embodiment is also very advantageous for tensile loaded plasters.

In all the embodiments shown in the drawings, bag-like foils or films can be provided between the active substance formulation and the matrix for further defining the active substance depots and better bounding the active substance liquid.

I claim:

1. A transdermal therapeutic system for the controlled administration of active substance to the skin with a backing layer remote from the skin, an active substance depot, an active substance delivery control device controlling the delivery of the active substance through the system and a [contact] *pressure sensitive* adhesive fixing means for fixing the therapeutic system to the skin, characterized in that the active substance depot is a multichamber system, in which the chambers are interconnected by channels and are provided with active substance delivery control means.

2. Transdermal therapeutic system according to claim 1, characterized in that the chambers are arranged in one or more identical active substance distribution matrices.

3. Transdermal therapeutic system according to claim 2, characterized in that it has an uninterrupted skin-side [contact] *pressure sensitive* adhesive layer as a fixing means.

4. Transdermal therapeutic system according to claim 3, characterized in that it also has one or more [contact] *pressure sensitive* adhesive layers between the backing layer and fixing means.

5. Transdermal therapeutic system according to claim 4, characterized in that the active substance is in liquid form.

6. Transdermal therapeutic system according to claim 5, characterized in that the multichamber system has desired breaking lines between the individual active substance chambers.

7. Transdermal therapeutic system according to claim 6, characterized in that the channels between the chambers have an internal diameter such that they only permit a through-flow of the active substance fluid upon application of pressure thereto.

8. Transdermal therapeutic system according to claim 7, characterized in that the multichamber system is a system of channels.

9. Transdermal therapeutic system according to claim 8, characterized in that the chambers are arranged at different height levels.

10. Transdermal therapeutic system according to claim 1, wherein the chambers are each provided with different active substance delivery control means.

11. Transdermal therapeutic system according to claim 2, characterized in that it has an interrupted skin-side [contact] *pressure sensitive* adhesive layer as a fixing means to the skin.

12. Transdermal therapeutic system according to claim 4, characterized in that the active substance is in solution.

13. Transdermal therapeutic system according to claim 5, characterized in that the multichamber system has desired breaking lines between the individual active substance chambers and in the backing layer.

14. Transdermal therapeutic system according to claim 13, further characterized in that the multichamber system has desired breaking lines also in other layers.

15. Transdermal therapeutic system according to claim 9, characterized in that the chambers are arranged at different height levels and in different distribution matrices.

* * * * *